US005780045A

United States Patent [19]

McQuinn et al.

[11] Patent Number: 5,780,045
[45] Date of Patent: Jul. 14, 1998

[54] TRANSMUCOSAL DRUG DELIVERY DEVICE

[75] Inventors: Roy L. McQuinn, Lake Elmo; Joan K. Barkhaus, Minneapolis, both of Minn.

[73] Assignee: Minnesota Mining and Manufacturing Company, St. Paul, Minn.

[21] Appl. No.: 746,353

[22] Filed: Nov. 8, 1996

Related U.S. Application Data

[63] Continuation of Ser. No. 885,282, May 18, 1992, abandoned.

[51] Int. Cl.$^6$ .................................................... A61F 13/02
[52] U.S. Cl. ........................ 424/434; 424/435; 424/436
[58] Field of Search .................................. 424/435, 430, 424/436, 434

[56] References Cited

U.S. PATENT DOCUMENTS

| | | | |
|---|---|---|---|
| 3,339,546 | 9/1967 | Chen et al. | 128/156 |
| 3,552,929 | 1/1971 | Fields et al. | 23/253 |
| 4,153,661 | 5/1979 | Ree et al. | 264/120 |
| 4,190,060 | 2/1980 | Greenleaf et al. | 128/760 |
| 4,253,460 | 3/1981 | Chen et al. | 128/283 |
| 4,292,299 | 9/1981 | Suzuki et al. | 424/16 |
| 4,321,252 | 3/1982 | Keith et al. | 424/28 |
| 4,373,519 | 2/1983 | Errede et al. | 128/156 |
| 4,444,193 | 4/1984 | Fogt et al. | 128/632 |
| 4,470,814 | 9/1984 | Chang et al. | 433/168 |
| 4,551,490 | 11/1985 | Doyle et al. | 524/22 |
| 4,573,996 | 3/1986 | Kwiatek et al. | 604/897 |
| 4,615,697 | 10/1986 | Robinson | 604/890 |
| 4,638,043 | 1/1987 | Szycher et al. | 528/75 |
| 4,668,232 | 5/1987 | Cordes et al. | 604/897 |
| 4,706,676 | 11/1987 | Peck | 128/632 |
| 4,740,365 | 4/1988 | Yukimatsu et al. | 424/435 |
| 4,764,378 | 8/1988 | Keith et al. | 424/435 |
| 4,772,470 | 9/1988 | Inoue et al. | 424/435 |
| 4,795,436 | 1/1989 | Robinson | 424/422 |
| 4,906,378 | 3/1990 | Hagen et al. | 210/635 |
| 4,909,256 | 3/1990 | Peck | 128/632 |
| 4,960,467 | 10/1990 | Peck | 106/209 |
| 4,981,145 | 1/1991 | Goldstein | 128/760 |
| 5,056,521 | 10/1991 | Parsons et al. | 128/635 |

FOREIGN PATENT DOCUMENTS

| | | |
|---|---|---|
| 304536 | 3/1989 | European Pat. Off. . |
| 56-068608 | 6/1981 | Japan . |
| 90/02511 | 3/1990 | WIPO . |

OTHER PUBLICATIONS

Chem. Abstracts 99:93643u.

*Primary Examiner*—Raj Bawa
*Attorney, Agent, or Firm*—MarySusan Howard; Walter N. Kirn; Ted K. Ringsred

[57] ABSTRACT

A transmucosal drug delivery device in the form of a sheet material. The device contains an acid-containing particulate polymeric resin dispersed throughout a polytetrafluoroethylene support matrix.

16 Claims, No Drawings

TRANSMUCOSAL DRUG DELIVERY DEVICE

This is a continuation of application Ser. No. 07/885,282 filed May 18, 1992, abandoned.

BACKGROUND OF THE INVENTION

1. Field of the Invention

This invention relates to mucosal adhesives. In another aspect this invention relates to compositions that adhere to oral mucosa. In yet another aspect this invention relates to methods of transmucosal drug delivery.

2. Description of the Related Art

Buccal tablets and like devices are known and disclosed for example in U.S. Pat. Nos. 4,740,365 and 4,764,378. These devices adhere to mucosal surfaces and dissolve or otherwise disintegrate over time, thus delivering drug into the mouth of the patient in a sustained fashion. It is also known that delivery of drugs across the oral mucosa avoids hepatic first-pass inactivation, inactivation by gastro-intestinal fluids, and other modes of inactivation characteristic of oral drug ingestion. Sustained release adhesive bandages, patches, and the like that contain drugs and adhere to mucosal surfaces are known to the art.

SUMMARY OF THE INVENTION

This invention provides a transmucosal drug delivery device in the form of a sheet material having a surface intended to be adhered to a mucosal surface, comprising:

1) a particulate polymeric resin comprising carboxylic acid containing monomer units and having an average particle size of less than or equal to about 100 μm;

2) from about 10 parts to about 200 parts by weight of a polytetrafluoroethylene support matrix based on 100 parts by weight of the resin; and 3) an amount of a drug effective to provide a desired therapeutic result;

which composition contains less than about 10% water by weight based on the weight of the polymeric resin, and adheres to a mucosal surface for a time sufficient to release the drug to the mucosal surface.

A device of this invention exhibits good adherence to human oral mucosa. Also, the drug is released in sustained fashion over a prolonged period to a mucosal surface or to the vicinity of a mucosal surface for, for example, local or systemic treatment.

In a preferred embodiment the device further comprises a flexible film backing adhered to one side of the device.

This invention also provides therapeutic methods. One such method is a method of achieving and/or maintaining a therapeutically effective blood level of a drug in a mammal, comprising the steps of:

a) adhering a device of the invention to a mucosal surface of a mammal; and b) allowing the device to remain adhered for a time sufficient to release the drug such that a therapeutically effective blood level of drug is achieved and/or maintained.

Another such method is a method of delivering a drug to a mucosal surface of a mammal or to the vicinity of a mucosal surface of a mammal to provide a therapeutic effect on or in the vicinity of the mucosal surface, which method comprises the steps of:

a) adhering a device of the invention to the mucosal surface;

b) allowing the device to remain adhered for a time sufficient to release the drug to the mucosal surface or to the vicinity of the mucosal surface to provide the desired therapeutic effect.

A device of the invention can be used to administer drugs systemically (e.g., across the oral or vaginal mucosa or other mucosal surfaces) or locally (e.g., to the oral or vaginal cavity). A device of the invention exhibits sustained delivery of basic, acidic, and neutral drugs, and salts thereof and allows the delivery rate to be tailored as desired. In the case of delivery of a drug across the oral mucosa, a device of the invention can also minimize the loss of a drug to the gastro-intestinal tract. A device of the invention is also soft and conformable such that it can be worn comfortably by the user.

DETAILED DESCRIPTION OF THE INVENTION

The polymeric resin component of a device composition of the invention comprises monomer units containing carboxylic acid moieties. The resin preferably comprises at least about 55% by weight of carboxylic acid moieties based on the total weight of the resin. Suitable carboxylic acid-containing monomers include acrylic acid, maleic acid, itaconic acid, citraconic acid, methacrylic acid, and the like, and combinations thereof. Acrylic acid is preferred. The polymeric resin can also comprise minor amounts (e.g., less than about 20 percent by weight based on the total weight of all monomers in the polymer) of comonomers that are polymerizable with the carboxylic acid-containing monomer, such as methyl vinyl ether, lower alkyl (meth)acrylates, and the like.

Linear polyacrylic acid resins with a molecular weight between about 400,000 and about 5,000,000 have been found to be suitable for use in a composition of the invention. More preferred, however, are crosslinked resins. Most preferred resins include those comprising polyacrylic acid with a molecular weight between about 750,000 and about 4,000,000, preferably about 2,000,000 to about 4,000,000, and more preferably about 3,000,000, crosslinked with about 0.75% to about 2% by weight, based on the total weight of the resin, of a polyalkenyl polyether such as an allyl ether of sucrose or an allyl ether of pentaerythritol. Particularly preferred resins of this type include the resins available under the trade designation CARBOPOL™ resin (e.g., CARBOPOL™ resins 910, 934, 934P, 941, 951, and 1342 from B.F. Goodrich Co., Specialty Polymers and Chemical Division, Cleveland, Ohio). CARBOPOL™ 934P resin is most preferred, as it is generally recognized as acceptable for pharmaceutical applications. Another suitable resin is "polycarbophil", a material commercially available from A. H. Robins Co., Richmond, Va., and described in USP XX as a polyacrylic acid crosslinked with divinylglycol.

A polyacrylic acid resin or a crosslinked resin such as those enumerated above can be partially neutralized by a base of an alkali metal, or by a base of a divalent or trivalent metal (e.g., $Zn^{+2}$, $Ca^{+2}$, $Mg^{+2}$, or $Al^{+3}$). Basic polyamines such as EUDRAGIT™E (a copolymer of dimethylaminoethyl methacrylate and neutral methacrylates, available from Rohm Pharma, Weiterstadt, Germany) are also suitable for use in neutralizing a resin. In such a resin, up to about 30% of the carboxylic acid moieties in the resin can be neutralized by a base. Preferred bases include $Al(OH)_3$ and $Ca(OH)_2$.

It is preferred that the resin have an average particle size of between about 1 μm and about 80 μm, more preferably between about 1 μm and about 30 μm, and most preferably between about 2 μm and about 10 μm.

It is desirable to keep the level of moisture low in a device of the invention. A device of the invention has a water content of less than about 10% by weight, preferably less than about 6%, more preferably less than about 4% by weight, and most preferably less than about 2% by weight based on the total weight of the resin. In order for the composition to have the requisite low water content the resin, prior to incorporation in the composition, is preferably dried to the desired level and protected from ambient moisture. Once the resin is incorporated in a composition of the invention, ambient moisture is no longer generally of concern, as the resin, which is generally hygroscopic, is protected from ambient moisture by the support matrix (described below). A device can be stored for at least several months at ambient humidity without adversely affecting its adhesive properties.

By itself, a polymeric resin as described above generally possesses insufficient structural integrity. Such acidic resins can also be irritating to mucosal tissue. Further, a resin alone provides no means of controlled hydration and sustained release of drug. To remedy these deficiencies, device further comprises a polytetrafluoroethylene support matrix. The resin is preferably substantially dispersed throughout the polytetrafluoroethylene support matrix.

The relative amounts of the polymeric resin and the polytetrafluoroethylene support matrix can affect both the duration of adhesion and the drug release properties of a composition of the invention. Generally a composition of the invention comprises about 10 parts to about 200 parts, preferably about 10 parts to about 100 parts, and most preferably 15 to about 50 parts by weight of a polytetrafluoroethylene support matrix, based on 100 parts by weight of the resin.

The support matrix is preferably in the form of a polytetrafluoroethylene (PTFE) web. Such webs having particulate material substantially uniformly dispersed therein are disclosed in, e.g. U.S. Pat. Nos. 4,153,611 (Ree et al.), 4,373,519 (Errede et al.), and 4,906,378 (Hagen et al.), the disclosures of which are incorporated herein by reference. The polytetrafluoroethylene web is soft such that the device can be worn without significant discomfort to the user.

A device of the invention also comprises a drug. Drugs that can be delivered include those useful for the local treatment of the mouth or throat, or the vaginal cavity, in addition to those useful for systemic treatment via delivery through mucosal tissue. They include antiinflammatory drugs, both steroidal (e.g., hydrocortisone, prednisolone, triamcinolone) and nonsteroidal (e.g., naproxen, piroxicam); bacteriostatic agents (e.g., chlorhexidine, hexylresorcinol); antibacterials (e.g., penicillins such as penicillin V, cephalosporins such as cephalexin, erythromycin, tetracycline, gentamycin, sulfathiazole, nitrofurantoin, and quinolones such as norfloxacin, flumequine, and ibafloxacin); antiprotazoals (e.g., metronidazole); antifungals (e.g., nystatin); coronary vasodilators (e.g., nitroglycerin); calcium channel blockers (e.g., nifedipine, diltiazem); bronchodilators (e.g., theophylline, pirbuterol, salmeterol, isoproterenol); enzyme inhibitors such as collagenase inhibitors, protease inhibitors, elastase inhibitors, lipoxygenase inhibitors (e.g., A64077), and angiotensin converting enzyme inhibitors (e.g., captopril, lisinopril); other antihypertensives (e.g., propranolol); leukotriene antagonists (e.g., ICI204,219); anti-ulceratives such as H2 antagonists; steroidal hormones (e.g., progesterone, testosterone, estradiol); antivirals and/or immunomodulators (e.g., 1-isobutyl-1H-imidazo[4,5-c]quinolin-4-amine, 1-(2-hydroxy-2-methylpropyl)-1H-imidazo[4,5-c]quinoline -4-amine, and other compounds disclosed in U.S. Pat. No. 4,689,338, incorporated herein by reference, acyclovir); local anesthetics (e.g., benzocaine, propofol); cardiotonics (e.g., digitalis, digoxin); antitussives (e.g., codeine, dextromethorphan); antihistamines (e.g., diphenhydramine, chlorpheniramine, terfenadine); narcotic analgesics (e.g., morphine, fentanyl, buprenorphine); peptide hormones (e.g., human or animal growth hormones, LHRH); cardioactive products such as atriopeptides; proteinaceous products (e.g., insulin); enzymes (e.g., antiplaque enzymes, lysozyme, dextranase); antinauseants (e.g., scopolomine); anticonvulsants (e.g., carbamazine); immunosuppressives (e.g., cyclosporine); psychotherapeutics (e.g., diazepam); sedatives (e.g., phenobarbital); anticoagulants (e.g., heparin); analgesics (e.g., acetaminophen); antimigraine agents (e.g., ergotamine, melatonin, sumatripan); antiarrhythmic agents (e.g., flecainide); antiemetics (e.g., metaclopromide, ondansetron); anticancer agents (e.g., methotrexate); neurologic agents such as anxiolytic drugs; hemostatics; anti-obesity agents; and the like, as well as pharmaceutically acceptable salts and esters thereof.

The drug is present in a therapeutically effective amount, which will depend upon the particular drug used, the intended therapy, and the desired duration of use of a particular individual device containing the drug. Practical limitations on the amount of drug are that amount above which the composition begins to lose adhesion to a mucosal surface, and that amount below which a therapeutically effective blood level of drug cannot be achieved and/or maintained. Generally, the preferred range is from about 0.1% to about 25% by weight based on the total weight of the device. Preferably, the drug will be capable of release from the device in a sustained fashion over a prolonged period (i.e., at least about 6 hours and preferably at least about 12 hours).

A device of the invention preferably comprises a flexible film backing on one side of the device. The backing is preferably a flexible film that prevents bulk fluid flow and is inert to the ingredients of the device. The backing protects the composition from excessive swelling and loss of adhesion over the time period during which the composition is intended to remain adhered to the mucosal surface. In the case of a device that contains a drug intended to be delivered to or across a mucosal surface (as opposed to delivery to the vicinity of the mucosal surface, e.g., to the oral cavity), the film backing material is preferably substantially impermeable to the drug and therefore it effectively prevents migration of the drug out of the coated portion of the device. In the case of a device that contains a drug intended to be delivered, e.g., to the oral cavity or the vaginal cavity, the backing can be permeable to the agent to be delivered and can be permeable to saliva as well.

The backing can be any of the conventional materials used as backing for tapes or dressings, such as polyethylene, polypropylene, ethylene-vinyl acetate copolymer, ethylene propylene diene copolymer, polyurethane, rayon, and the like. Non-woven materials such as polyesters, polyolefins, and polyamides can also be used. Also, a layer of a hydrophobic elastomer such as polyisobutylene can function as a backing. Preferred backing materials include an acrylate pressure-sensitive adhesive coated polyurethane film such as TEGADERM™ brand surgical dressing (commercially available from the 3M Company, St. Paul, Minn.).

The most preferred flexible film backings occlude substantially all of the surface area of the patch other than that surface that is intended to be adhered to the mucosal surface, while the surface of the patch that is to be adhered to the mucosal surface is substantially free of the backing. When the device is in use there is substantially no uncoated surface area of the device (such as uncoated sides or edges) exposed to mucus into which the drug can be delivered inadvertently.

The most preferred backing materials are also substantially insoluble in mucus and other fluids endogenous to the mucosal surface (e.g., in a device intended to adhere to buccal mucosa or other oral mucosa the backing is substantially insoluble in saliva). "Substantially insoluble" as used herein means that a thin coating (e.g., 0.1 mm thick) of the film backing material will not be eroded such that areas become exposed when a device is in place on a mucosal surface for a period of several hours.

The most preferred film backing materials include those that can be taken up in solution or suspension and applied (e.g., by brushing, spraying, or the like) from solution or suspension, and those that can be applied in the form of liquid prepolymeric systems and subsequently cured. These preferred film backing materials include polymeric materials and polymeric systems that are commonly used as enteric coatings or controlled release coatings. Exemplary materials include cellulose derivatives (e.g., ethylcellulose, cellulose acetate butyrate, cellulose acetate, cellulose acetate phthalate, hydroxypropyl methylcellulose phthalate, chitin, chitosan), polyvinyl alcohol and derivatives thereof such as polyvinyl acetate phthalate, shellac, zein, silicone elastomers, and polymethacrylates (e.g., cationic polymers based on dimethylaminoethyl methacrylate such as those copolymers available as EUDRAGIT™ type E, L, and S copolymers, copolymers of acrylic and methacrylic acid esters containing quaternary ammonium groups such as those copolymers available as EUDRAGIT™ type RS and RL copolymers, and others known to those skilled in the art). Most preferred backing materials include zein and ethylcellulose.

A device can contain other ingredients, for example excipients such as flavorings or flavor-masking agents, dyes, penetration enhancers, water-soluble or water-swellable fibrous reinforcers, and the like under circumstances and in amounts easily determined by those skilled in the art. Penetration enhancers have particular utility when used with drugs such as peptides and proteins. Suitable penetration enhancers include anionic surfactants (e.g., sodium lauryl sulfate); cationic surfactants (e.g., cetylpyridinium chloride); nonionic surfactants (e.g., polysorbate 80, polyoxyethylene 9-lauryl ether, glyceryl monolaurate); lipids (e.g., oleic acid); bile salts (e.g., sodium glycocholate, sodium taurocholate); and related compounds (e.g., sodium tauro-24,25-dihydrofusidate).

A resin useful in a composition of this invention can be prepared using conventional procedures and conventional laboratory equipment. For example, such resins can be prepared from acrylic acid and the appropriate crosslinkers by methods well known to those skilled in the art, and disclosed for example in U.S. Pat. No. 2,798,053 (Brown). A commercially available polyacrylic acid resin or a commercially available particulate resin such as the CARBOPOL™ resins discussed above can be used as received if it is available in an appropriate particle size and with a suitably low water content.

Conventional drying methods, preferably using temperatures less than about 95° C., and more preferably less than about 50° C., can be used to dry a resin to the desired degree, e.g., less than about 2% water content. Further, if it is desired to increase or decrease the particle size, a resin can be wet-granulated by first wetting and stirring with a polar solvent (e.g., isopropyl alcohol), drying to the desired degree (e.g., in a tray oven), and then milling to a powder of the desired size. Particle size can also be adjusted by other conventional techniques, with the caveat that substantial degradation of the resin is to be avoided.

A neutralized resin as discussed above can be prepared as described in Patent Application WO 90/06505, incorporated herein by reference.

A drug, a suitable resin, and any excipient or other ingredient can be formulated into a device according to the general methods set forth in U.S. Pat. No. 4,153,661 (Ree et al.), incorporated herein by reference. The methods disclosed in said patent involve the use of an aqueous PTFE formulation. The use of an aqueous PTFE formulation, however, results in severe swelling of the resin and the composition sticks to the mill roll when it is milled. Moreover, as devices of the invention contain less than about 10 percent by weight water based on the weight of the resin, drying to the desired level can be difficult and/or time consuming. Accordingly, it is preferred to use a method that avoids the use of water or a solvent that swells the resin. A preferred method involves combining the resin, the drug, and any excipient or other ingredient with dry PTFE particles having an average particle size of about 300 μm to about 1000 μm. A drug and any excipient or other ingredient can be incorporated by first adding it and then the resin, or vice versa, to the PTFE particles. In the alternative the drug and any excipient or other ingredient can be incorporated by first adsorbing it on the resin or on an inert support such as silica, absorbing it into the resin, or ionically bonding it to the resin. Sufficient inert liquid to form a putty-like mass can then be added. Preferably, about 100 parts by weight of the resin is used, about 40 parts by weight of the PTFE is used, and about 500 parts by weight of the inert liquid is used. Suitable liquids include chlorofluorocarbon and fluorocarbon liquids. Fluorocarbon liquids such as FLUORINERT™ FC5312 electronic fluid (3M) are preferred.

The resulting mixture is then stirred until it is of dough-like consistency and processed in a rubber mill as generally described in U.S. Pat. No. 4,153,661. Generally the processing involves biaxial fibrillation of the PTFE by repeatedly passing the mixture between the calendering rolls of the rubber mill. After each individual pass the resulting sheet is folded parallel to the axis of the calendering rolls into a layered structure, preferably a three-layered structure, rotated 900 and passed again through the calendering rolls. Preferably about 10 to about 20 passes are carried out in order to form a PTFE web having the resin substantially dispersed throughout. The resulting sheet is then passed through the rolls as required in order to form a sheet of the desired thickness. Once a sheet of the desired thickness is made, it can be air-dried at room temperature or placed in a convection oven at an appropriate temperature in order to remove the excess inert liquid. The final dry sheet device is preferably 0.2 mm to about 2 mm thick.

The flexible film backing can be applied using methods well known to those skilled in the art. A device in the form of a sheet material with a backing applied thereto can be made into a patch with a backing by die-cutting individual patches from the sheet. A patch can be of any suitable size and shape, e.g., a 1 cm$^2$ circular disk. In the case of a device having a backing applied from solution or suspension, individual patches can be arranged on a coating surface such that the portion of the patch that is intended to be adhered to the mucosa is in contact with the coating surface. The film backing material can be applied to the remainder of the patch by spraying, brushing or otherwise applying the film backing material.

While devices of the invention adhere to mucosal surfaces, they preferably exhibit substantially no instantaneous adhesion to dry skin. A device or a patch of the invention can therefore be handled by a patient without undue concern that the device or patch will have its mucosal adhesive properties compromised by adhering to the skin or to another dry surface prior to placement on the mucosa.

A device of the invention can be applied to a mucosal surface, such as the oral mucosa, e.g., the buccal mucosa or gingival mucosa, of a mammal and replaced as desired (e.g., as is necessary or as is convenient to the user) with a fresh patch, e.g., to maintain a therapeutically effective blood level of a drug. A device or a patch of the invention exhibits sustained release of a drug such that a therapeutically effective blood level of the drug can be achieved and/or maintained in a mammal for an extended period of time. Also, a therapeutic level of drug can be maintained in the vicinity of the mucosal surface (e.g., in the oral cavity or the vaginal cavity) if the treatment being effected is local rather than systemic.

Example 1

CARBOPOL™ 910 resin (50 g; B. F. Goodrich) was mixed with 16.7 g of PTFE (TEFLON™ 6-C polytetrafluoroethylene, DuPont) and 250 g of FLUORINERT· 5312 electronic liquid (3M) to afford a substantially homogeneous putty-like mass. This mass was further mixed by hand with a spatula for about 1 minute. The mass was then formed into a film by 15 successive passes between steel calendering rolls (15 cm in diameter, 28 cm long) at 50° C. using a nip gap of about 4 mm. After each pass, the resulting substantially rectangular film was z-folded parallel to the axis of the calendaring rolls and rotated 90° prior to the next pass. After these 15 initial passes the film was again repeatedly passed through the rolls, beginning with a nip gap of about 4 mm and closing the nip gap about 0.65 mm on each successive pass until the final sheet was about 0.3 mm thick. The final sheet was air-dried at room temperature to remove the excess liquid. Patches of about 1 cm² area were cut from the sheet with a 1 cm² circular die.

A flexible film backing was applied to several of the patches by spraying a 10% zein in ethanol/water solution directly on one side of the patch. The coated patches as well as patches without a backing were applied to the oral mucosa (the inside lip or to the gum) of several beagle dogs and visually observed at frequent intervals throughout the next 24 hours. All patches adhered equally well initially. By 2–3 hours post application, the patches without backings had swollen to 3–4 times greater size than the patches with backings and had become translucent due to the large amount of absorbed water. By about 4 hours post application, the patches without backings had either fallen off the mucosa or were very loose and about to fall off. In contrast, the patches with backings were still very firmly attached to the tissue and they still retained their original opaque appearance. All of the patches with backings (4/4) were firmly adhered at 12 hours post application and two of them were still attached at 24 hours post application.

These results show that these placebo patches adhere to oral mucosa. These results also show that the presence of a backing improves adhesion and structural integrity.

Example 2

Using the general method of Example 1, except that ethanol was used in place of the FLUORINERT electronic liquid, sheet material containing approximately 10% by weight PTFE, 85% by weight "polycarbophil", and 15% by weight theophylline was prepared. The theophylline was incorporated by premixing with the polycarbophil.

The resulting sheet (approximately 15 cm long, 9 cm wide and 4.3 mm thick) was relatively stiff. The sheet was made more pliable by placing it in a dry glass dish and incubating it in the humid atmosphere of a covered water bath for about 2 to 3 hours.

In-vitro Dissolution

Three rectangular (8 mm by 10 mm) samples, each weighing approximately 167 mg, were cut from the sheet material. Each sample was weighted with a paper clip then placed in a vessel in a USP 2 dissolution apparatus. Each vessel was filled with 1000 mL of deionized, deaerated water and the paddle speed was set at 50 rpm. Samples were withdrawn at 1, 2, 4, 6, 8, 12, 16 and 20 hours. Theophylline content was determined by measuring absorbance at 271 nm. The table below shows the percent dissolved theophylline (assuming each sample contained approximately 25 mg of theophylline) at each time point. The values are the average of the values for the three vessels. The standard deviation is given for each entry.

| Time (hr) | % Dissolved |
| --- | --- |
| 1 | 40.2 ± 0.92 |
| 2 | 56.4 ± 1.22 |
| 4 | 74.8 ± 0.64 |
| 6 | 80.1 ± 1.05 |
| 8 | 81.4 ± 0.74 |
| 12 | 81.7 ± 0.80 |
| 16 | 81.9 ± 1.16 |
| 20 | 81.7 ± 1.88 |

In-vivo Delivery

The in-vivo drug delivery of the material was assessed in two female beagle dogs. Patches of 1.5 cm diameter and weighing 350 mg were cut from the sheet with a circular die. The patches had no occlusive backing so both sides were adherent. Both dogs were dosed (two patches for Dog A and one patch for Dog B) by applying the patches to the mucosal side of the lip just opposite the upper canine teeth. The patches adhered tightly and almost instantly. Venous blood samples (3 to 4 mL) were obtained from each dog at 0.5, 1, 2, 3, 4, 5, 6, 8 and 24 hours post dose. Plasma was separated from whole blood and stored frozen in glass vials until analysis. The dogs were fasted for about 16 hours prior to dosing and for about 6 hours post dosing; water was allowed ad libitum. The patches began to noticeably hydrate by 1 hour post dose. They swelled to approximately three times their original size. In Dog A, one of the two applied patches fell out between 6 and 8 hours post dose. At 8 hours post dose, the patch remaining in Dog A was removed. The patch in Dog B was removed at 24 hours post dose. No signs of irritation were noted in either dog's mouth.

Plasma concentrations of theophylline were determined by TDx™ assay (Abbott Laboratories). The results are given in the table below. A plasma level indicated as "low" means that the concentration of the detected substance is below the sensitivity of the assay and the identity of the substance detected is ambiguous.

Theophylline Plasma Levels (μg/mL)

| Time (hr) | Dog A | Dog B |
|---|---|---|
| 0.5 | 0.46 | 0.6 |
| 1 | 0.81 | 0.8 |
| 2 | 1.93 | 1.1 |
| 3 | 1.85 | 0.78 |
| 4 | 2.58 | 1.71 |
| 5 | 3.26 | 1.79 |
| 6 | 4.06 | 1.84 |
| 8 | 2.96 | 2.31 |
| 24 | Low | 1.71 |

The results set forth above show that a drug delivery device of the invention will release theophylline at a controlled rate and that a therapeutically effective blood level of theophylline can be obtained with a device without a backing.

Example 3

Using the general method of Example 2, sheet material was prepared which contained 4% by weight of digoxin, 20% by weight of PTFE and 76% by weight of CARBOPOL™ 910 resin.

In-vivo Delivery

The in-vivo drug delivery of the material was assessed in three female beagle dogs. Patches of 1.2 cm diameter and weighing approximately 26 mg were cut from the sheet with a die. The patches had no occlusive backing so both sides were adherent. All three dogs were dosed by applying a patch to the mucosal side of the upper lip next to the gums in the front of the muzzle. Venous blood samples (about 4 mL) were obtained from each dog prior to dosing and at 1, 2, 3, 4, 6, 8, 10, 12, 24 and 28 hours post dose. Plasma was separated from whole blood and stored frozen in glass vials until analysis. The dogs were not allowed food for 6 hours post dosing; water was allowed ad libitum. In Dog A it was noted that at 2 hours post dose the patch had slid down about halfway onto a tooth. Dog A spit out the patch between 2 and 3 hours post dose. The patch was replaced. The second patch was spit out between 8 and 10 hours post dose and was not replaced. Emesis was noted in Dog B between 2 and 3 hours post dose. Dog B spit out the patch between 6 and 8 hours post dose; it was not replaced. Dog C spit out the patch between 4 and 6 hours post dose; it was not replaced.

Plasma concentrations of digoxin were determined by TDx™ assay (Abbott Laboratories). A plasma level indicated as "low" means that the concentration of the substance detected is below the sensitivity of the assay and the identity of the substance is ambiguous. The lowest concentration on the standard curve was 0.2 ng/mL.

Digoxin Plasma Levels (ng/mL)

| Time | Dog A | Dog B | Dog C |
|---|---|---|---|
| 0 | low | low | low |
| 1 | 0.49 | low | low |
| 2 | 0.65 | 0.08 | 0.02 |
| 3 | 0.55 | 0.07 | 0.16 |
| 4 | 0.73 | 0.12 | low |
| 6 | 0.47 | 0.21 | 0.14 |
| 8 | 0.42 | 0.12 | 0.03 |
| 10 | 0.44 | 0.16 | low |
| 12 | 0.31 | 0.00 | low |
| 24 | 0.22 | 0.01 | low |
| 28 | 0.16 | 0.10 | low |

The results show that a therapeutically effective blood level of digoxin can be obtained with a device without a backing.

What is claimed is:

1. A method of delivering a drug to a mucosal surface of a mammal or to the vicinity of a mucosal surface of a mammal to provide a therapeutic effect on or in the vicinity of the mucosal surface, which method comprises the steps of:
   a) adhering to the mucosal surface a transmucosal drug delivery device in the form of a sheet material having a surface comprising:
      1) a particulate polymeric resin comprising carboxylic acid containing monomer units and having an average particle size of less than or equal to about 100 mm;
      2) from about 10 parts to about 200 parts by weight of a polytetrafluoroethylene support matrix based on 100 parts by weight of the resin; and
      3) an amount of a drug effective to provide a desired therapeutic result;
   which composition contains less than about 10% water by weight based on the weight of the polymeric resin, and adheres to a mucosal surface to release the drug to the mucosal surface;
   b) allowing the device to remain adhered so as to release the drug to the mucosal surface or to the vicinity of the mucosal surface.

2. The method according to claim 1 wherein the transmucosal drug delivery device further comprises a flexible film backing on one side of the device.

3. The method according to claim 2, wherein the flexible film backing is impermeable to the drug.

4. The method according to claim 2, wherein the flexible film backing occludes all of the surface area of the patch other than that surface that is intended to be adhered to the mucosal surface.

5. The method according to claim 2, wherein the flexible film backing is insoluble in fluids endogenous to the mucosal surface.

6. The method according to claim 2, wherein the flexible film backing is selected from the group consisting of celluloses, polyvinyl alcohols, shellac, zein, a silicone elastomer, a polymethacrylate, and a copolymer of acrylic and a methacrylic acid ester containing quaternary ammonium groups.

7. The method according to claim 6, wherein the flexible film backing is zein or ethylcellulose.

8. The method according to claim 1, wherein the resin contains at least about 55% by weight of carboxylic acid moieties based on the total weight of the resin.

9. The method according to claim 1, wherein the monomer is acrylic acid, maleic acid, itaconic acid, citraconic acid, or methacrylic acid, or a combination thereof.

10. The method according to claim 1, wherein the monomer is acrylic acid.

11. The method according to claim 1, wherein the resin has an average particle size of between about 1 mm and about 80 mm.

12. The method according to claim 1, wherein the resin has an average particle size of between about 1 mm and about 30 mm.

13. The method according to claim 1, wherein the resin has an average particle size of between about 2 mm and about 10 mm.

14. The method according to claim 1, wherein the resin has a water content of less than about 6% based on the total weight of the resin.

15. The method according to claim 1, wherein the device comprises about 10 parts to about 100 parts by weight of a polytetrafluoroethylene support matrix, based on 100 parts by weight of the resin.

16. The method according to claim 1, wherein said drug is delivered systemically across a mucosal surface.

* * * * *